United States Patent
Barclay et al.

(10) Patent No.: US 6,207,462 B1
(45) Date of Patent: Mar. 27, 2001

(54) MICROWAVE APPARATUS AND METHOD FOR ANALYSIS OF ASPHALT-AGGREGATE COMPOSITIONS

(75) Inventors: David Allan Barclay, Charlotte; Ali Regimand, Raleigh, both of NC (US)

(73) Assignee: CEM Corporation, Matthews, NC (US)

(*) Notice: Subject to any disclaimer, the term of this patent is extended or adjusted under 35 U.S.C. 154(b) by 0 days.

(21) Appl. No.: 09/187,854

(22) Filed: Nov. 6, 1998

Related U.S. Application Data (63) Continuation-in-part of application No. 09/045,392, filed on Mar. 20, 1998.

(51) Int. Cl.[7] .......................... G01N 31/12; G01N 33/26; H05B 6/64
(52) U.S. Cl. .......................... 436/155; 219/710; 219/712; 219/756; 219/757; 219/762; 422/68.1; 422/78; 422/99; 422/109; 436/55; 436/60; 436/139; 436/140; 436/141; 436/142; 436/143; 436/145; 436/157; 436/160; 436/181; 436/183
(58) Field of Search .......................... 436/55, 60, 139–141, 436/143, 145, 147, 155, 157, 160, 174, 181, 183; 422/68.1, 78, 99, 109, 288, 307; 219/697, 710, 712, 756, 757, 762

(56) References Cited

U.S. PATENT DOCUMENTS

Re. 34,373 * 9/1993 Collins et al. ................. 219/10.55 B
4,043,048    8/1977 Veater .

(List continued on next page.)

FOREIGN PATENT DOCUMENTS 2261827   6/1993 (GB) .

OTHER PUBLICATIONS

F. Parker Jr. J. Test. Eval. Mar. 1991, 19, 161–168.*

H. A. Todres et al. J. Test. Eval. Nov. 1994, 22, 564–570.*

E. R. Brown et al. Asphalt Paving Technol. 1995, 64, 241–277.*

S. Kocakusak et al. NATO ASI Ser., Ser E 1995, 282, 351–358.*

*Primary Examiner*—Arlen Soderquist
(74) *Attorney, Agent, or Firm*—Philip Summa, P.A.

(57) ABSTRACT

A method and apparatus are disclosed for analyzing the aggregate content of asphalt-aggregate compositions. The method includes placing a preheated, preweighed container carrying a sample of an asphalt-aggregate composition into a preheated furnace with the preheated furnace being warmer than the preheated sample, continuing to heat the furnace while drawing air through the furnace at a rate that avoids impeding the heating of the furnace or the sample until the sample in the container reaches its combustion temperature and the combustion of the sample becomes exothermic, initiating a second draw of air around rather than through the furnace to moderate the exterior temperature of the furnace, accelerating the draw through the furnace to increase the rate of combustion of the exothermic reaction, and reweighing the container and sample after combustion is complete. The apparatus includes a furnace, a housing around the furnace, a furnace exhaust in communication with the furnace, a housing exhaust in communication with the housing, means for drawing an airflow though the furnace and into the furnace exhaust, means for drawing a separate airflow though the housing and into the housing exhaust, and a junction between the exhausts that forms a common exhaust from the housing and the furnace.

42 Claims, 3 Drawing Sheets

U.S. PATENT DOCUMENTS

| | | |
|---|---|---|
| 4,164,655 | 8/1979 | Noma et al. . |
| 4,307,277 * | 12/1981 | Maeda et al. ................. 219/10.55 R |
| 4,525,854 | 6/1985 | Molbert et al. . |
| 4,565,669 * | 1/1986 | Collins et al. .......................... 422/78 |
| 4,849,020 | 7/1989 | Osborne et al. . |
| 4,874,950 | 10/1989 | Regimand . |
| 4,990,456 | 2/1991 | Loucks et al. . |
| 5,066,843 * | 11/1991 | Revesz .......................... 219/10.55 R |
| 5,151,601 | 9/1992 | Regimand . |
| 5,170,667 | 12/1992 | Takeuchi et al. . |
| 5,248,200 | 9/1993 | Walsh . |
| 5,279,971 * | 1/1994 | Schneider .............................. 436/139 |
| 5,318,754 * | 6/1994 | Collins et al. ....................... 422/109 |
| 5,365,043 * | 11/1994 | Bradford .............................. 219/710 |
| 5,378,878 * | 1/1995 | Revesz .................................. 219/762 |
| 5,558,029 | 9/1996 | Peake . |
| 5,620,659 * | 4/1997 | Revesz ................................... 422/90 |
| 5,796,080 * | 8/1998 | Jennings et al. ..................... 219/697 |
| 6,033,912 * | 3/2000 | Lautenschlager ...................... 436/55 |

\* cited by examiner

MICROWAVE APPARATUS AND METHOD FOR ANALYSIS OF ASPHALT-AGGREGATE COMPOSITIONS

This application is a continuation-in-part of Ser. No. 09/045,392 filed Mar. 20, 1998.

FIELD OF THE INVENTION

The present invention relates to the analysis of compositions formed of asphalt and aggregates such as crushed rock and sand. In particular, the invention relates to a method and apparatus for analyzing the percentage composition of asphalt in such compositions.

BACKGROUND OF THE INVENTION

Compositions formed of mixtures of asphalt and aggregates materials are one of the most widely used materials for paving roads and highways. Although the term "asphalt" is commonly used to refer to the road material, it more properly applies to the "tar" portion of a mixed composition of tar and aggregate. Thus, the asphalt is a dark brown or black cementitious material, which is solid or semi-solid in consistency, in which the predominating constituents are bitumens which occur in nature or are obtained as byproducts from petroleum refining. Asphalt is a mixture of paraffinic and aromatic hydrocarbons and heterocyclic compounds containing sulfur, nitrogen and oxygen. Asphalt is also referred to as "petroleum asphalt," "Trinidad pitch," or "mineral pitch." Asphalt is a black solid or viscous liquid that has a flash point of about 450° F. (232° C.), an auto-ignition temperature of about 900° F. (482° C.), and softens from its solid or semi-solid state to a viscous liquid at approximately 93° C. Other typical uses of asphalt include roofing, joint filling, special paints, adhesive and electrical laminates, and hot belt compositions, a dilutent in low-grade rubber products and a number of other applications. These and other properties and uses of asphalt are generally well known in the art and can be found, for example, in Lewis, *Hawley's Condensed Chemical Dictionary*, 12th Edition (1993).

In paving compositions, asphalt is typically present in an amount of about 5% by weight. With respect to such compositions, the percentage of asphalt and the nature and size of the aggregate material (typically rocks and sand) used to make the composition are important for the proper structure and characteristics of the final road structure. For example, typical roads are formed of three layers of asphalt and aggregate compositions. The bottom most layer includes rocks of one inch or greater average size, sand, and the asphalt. An intermediate layer generally includes a composition formed of somewhat smaller rocks, typically 0.5–1 inch in diameter, again with sand and asphalt. Finally, a top layer is usually applied which has the smallest rocks, typically 0.5 inches or less in diameter plus sand and tar.

Because the aggregate generally represents more than 90% of a hot asphalt mix, aggregate gradation (i.e., the different particle sizes that are present in the blend) profoundly influences the properties of the hot mix (such as air voids, workability, and the amount of asphalt binder required) and the resulting properties of the pavement (such as stiffness, stability, and durability) (e.g., Aljassar et al., Toward Automating Size-Gradation Analysis of Mineral Aggregate, Transportation Research Record, Issue Number: 1437, pp. 35–42 (1994)). In this regard, research on asphalt-aggregate compositions has become quite detailed, including for example quantifying the influence on resistance to rutting when rounded, smooth, sand-sized aggregate particles are replaced by rough, angular, porous particles while other aggregates and the total gradation remain unchanged (e.g., Perdomo, D. and Button, J. W., Identifying and Correcting Rut-Susceptible Asphalt Mixtures, Final Report, Texas Transportation Institute, Texas A&M University, Texas State Department of Highways & Public Transp, Federal Highway Administration, Report Number: Fhwa/Tx-91/1121-2F;Res Rept 1121-2F;TTI: 2-8-87/91-1121, Pag: 164p), or evaluating the effect of the amount of soil binder (i.e., the smallest aggregate particles) on the engineering properties of asphalt-treated paving materials (Ping, and Kennedy, *The Effects of Soil Binder and Moisture on Black Base Mixtures*, Texas University, Center for Highway Research, Austin, Texas State Department of Highways & Public Transp Report Number: FHWA/TX79/08+183-12 Intrm Rpt.;FCP 45C2-352 Pag: 127p (1997)). Aggregate gradation is frequently determined by the well-known and widely used sieve analysis method.

Accordingly, as these exemplary references indicate, depending upon the conditions under which a road is used (e.g., traffic patterns and weather conditions), the composition of any one or more of the asphalt layers must be carefully designed and monitored. Additionally, because the aggregate materials are typically taken from local quarries, and the manufacture of the composition is not an exact science, the asphalt and aggregate compositions must be frequently tested, both as they are being made and after they have been applied to a roadway, to make sure that they meet the appropriate requirements.

Thus, there exists a need for determining: (1) the weight percentage of asphalt; and (2) the aggregate size distribution in a given sample of an asphalt-aggregate composition. In one conventional method of analysis, the percentage of asphalt is determined by a solvent extraction technique which uses chlorinated hydrocarbons to separate the asphalt from the aggregate materials. Because the solvents are generally considered to raise a hazard to persons who are exposed to their vapors, the solvent testing is becoming more and more disfavored, and indeed is expected to eventually become prohibited under appropriate environmental regulation.

In a second conventional method, a weighed sample of the composition is placed into a furnace which is then heated until the asphalt in the composition ignites. The asphalt is then allowed to burn until it is entirely consumed after which the remaining aggregate is weighed. The difference between the starting and ending weight is a measure of the composition of asphalt in the composition.

There are, however, at least two problems with this conventional ignition technique. First, in conventional conduction and convection heating, the burning asphalt can carry the combustion to temperatures of up to 900° C., i.e., a state which is somewhat out of control. These extreme temperatures can cause particular problems in the equipment or in handling the hot material or even confining the resulting fire.

Second, and perhaps just as important, the extreme temperatures tend to degrade the physical characteristics of the aggregate in the mixture, including its size. Thus, because the aggregate remaining after the asphalt has been burned off is typically measured to determine whether it is of the proper size, the size degradation resulting from the conventional ignition test leads to a certain inaccuracy in measuring the sizes of aggregate in any given sample.

As another problem, if the aggregate contains carbonate compounds, the excessive heat can drive off carbon dioxide, thus changing both the chemical and physical characteristics of the aggregate. Finally, the conventional ignition techniques tend to cause a loss of "fine" aggregates—literally blowing them away—so that such fines are neither sized nor weighed, further acerbating the accuracy problem.

Accordingly, the need exists for a method of determining the amount of asphalt in an asphalt-aggregate combination which avoids the use of environmentally disfavored solvents, which more carefully controls the combustion and which avoids the breakdown in the aggregate materials that tends to result in improper sizing following such testing.

In co-pending parent application Ser. No. 09/045,392 an improved technique for asphalt-aggregate analysis is disclosed that takes advantage of the properties of microwave radiation to provide improved methods and apparatus for the combustion-based analysis of asphalt-aggregate mixtures. It has now been discovered that such apparatus and methods can be enhanced—and the time required for analysis greatly reduced—by additional control of the appropriate airflows, and by incorporating improved structural elements.

OBJECT AND SUMMARY OF THE INVENTION

Therefore, it is an object of the present invention to provide a method and apparatus for analyzing asphalt aggregate compositions that has the potential to be generally faster, more efficient, and more accurate than prior techniques.

The invention meets this object with a method of analyzing the aggregate content of asphalt-aggregate compositions, in which the method comprises heating a furnace with a preweighed container carrying a sample of an asphalt aggregate composition therein while drawing air through the furnace at a rate that avoids impeding the heating of the furnace or the sample until the sample in the container reaches its combustion temperature and the combustion of the sample becomes exothermic. At that point the method comprises accelerating the draw through the furnace to increase the rate of combustion of the exothermic reaction until the exothermic reaction is complete, and thereafter re-weighing the container and sample.

In another aspect, the step of heating the furnace comprises heating the furnace while drawing air through it at the rate that avoids impeding the heating of the furnace or the sample until the sample reaches a first predetermined steeping temperature, a which point the draw through the furnace is accelerated to increase the rate of combustion of the sample.

In another aspect, the method comprises heating a sample of an asphalt-aggregate composition to combustion in a furnace, drawing an airflow into, through and out of the furnace to promote the combustion of the asphalt in the composition; drawing a separate airflow past, but not through, the furnace to help moderate the exterior temperature of the furnace without interfering with the combustion therein, and blending airflow that has exited the furnace with the airflow that has passed to the exterior to thereby moderate the temperature of the furnace exited airflow.

In its apparatus aspects, the invention comprises a cavity for holding an asphalt-aggregate sample, means for introducing microwave radiation into the cavity, materials in the cavity for absorbing microwave radiation in converting the microwave radiation into heat, an afterburner in gasflow communication with the cavity, a first fan for drawing air through the cavity and through the afterburner, and a second fan for drawing air around the cavity to moderate the external temperature of the cavity and its immediate environment. In another aspect, the furnace system comprises a furnace, a housing around the furnace, a furnace exhaust in communication with the furnace, a housing exhaust in communication with the housing, means for drawing an airflow through the furnace and into the furnace exhaust, means for drawing a separate airflow through the housing and into the housing exhaust, and a junction between the two exhausts that forms a common exhaust from the housing and the furnace.

The foregoing and other objects and advantages of the invention and the manner in which the same are accomplished will become clearer based on the following detailed description taken in conjunction with the accompanying drawings in which:

DETAILED DESCRIPTION

Figure 1:
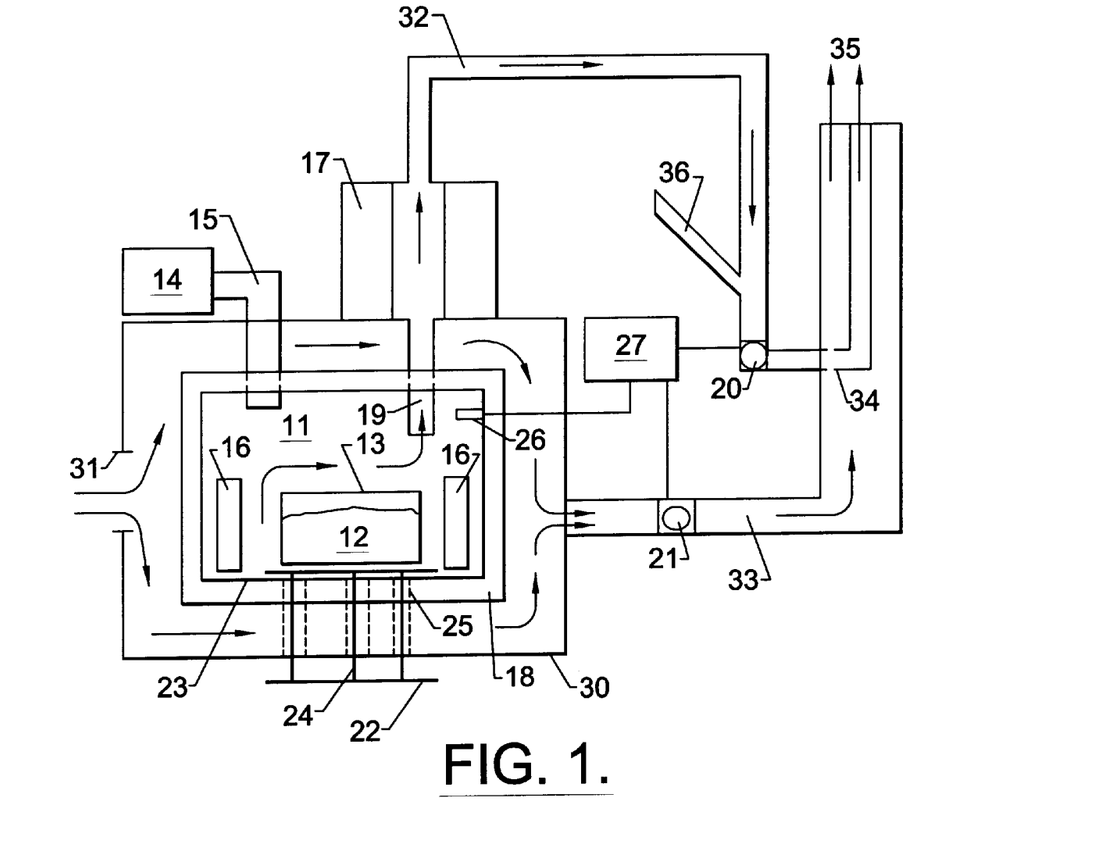
FIG. 1 is a cross-sectional schematic view of the invention.

The present invention is a method and associated apparatus for analyzing the aggregate content of asphalt-aggregate compositions. FIG. 1 is a cross-sectional schematic diagram that illustrates many of the method and apparatus aspects of the invention. The overall apparatus is broadly designated at 10 and includes a cavity 11 which is generally defined by the surrounding ceramic fibrous material 18 that is insulating with respect to conductive heat transfer and substantially transparent to microwave radiation. Although the term "furnace" can be applied to the entire apparatus 10, the term "furnace" is also used to describe the ceramic fibrous material 18. The particular use will be evident herein based on the context. The ceramic fibrous material 18 and the furnace structure it produces are quite similar to those referred to as "muffle" furnaces (e.g., U.S. Pat. No. 5,318,754 which is commonly assigned with the present invention) and will not otherwise be described in detail herein.

The cavity 11 holds an asphalt aggregate sample 12 which in preferred embodiments is maintained in a container 13. Means illustrated as the magnetron 14 and the waveguide 15 introduce microwave radiation into the cavity 11. Although microwave energy can be used to heat the sample 12 directly, in preferred embodiments, other materials illustrated as the susceptors 16, typically formed of a material such as silicon carbide, are placed in the furnace to absorb microwave radiation and convert it into heat energy which in turn heats the sample 12.

The apparatus 10 further comprises an afterburner 17 which in preferred embodiments comprises a tubular furnace, the nature and operation of which are generally well understood and will not be otherwise described in detail herein. The afterburner serves to complete the combustion of certain of the byproducts of the initial combustion of the sample 12 in the cavity 11. A first fan 20 draws air through the cavity 11, into a microwave choke 19, and through the afterburner 17. A second fan 21 draws air around, but not through the cavity 11 to moderate the external temperature of the cavity 11 and its immediate environment. The choke 19 is formed of a material that blocks microwave radiation (usually a metal) and has a length to diameter ratio that prevents microwaves from escaping into or through the afterburner. The length and diameter of the choke are selected based upon the wavelength of the microwaves produced by the source, using relationships that are well understood in this art.

Because the asphalt-content aspects of an the asphalt-aggregate analysis is generally based on weight loss, in preferred embodiments, the apparatus 10 further comprises a scale 22 in the cavity 11 for monitoring (preferably continuously) the weight of a sample 12 in the cavity 11. In preferred embodiments, and as illustrated in FIG. 1, the scale has a pan portion 23 in the cavity 11, and a series of supports 24 that extend downwardly from the pan through openings 25 in the furnace material 18. In this arrangement, many of the mechanical and electrical components of the scale can be positioned outside of the cavity 18 thus protecting them from the relatively harsh conditions, both of temperature and materials, that are generated in the cavity 11 during operation of the furnace. In the preferred embodiments, the support openings 25 also provide the entry point for airflow from the external surroundings into the cavity 11 and then to the afterburner as just described.

In preferred embodiments, the apparatus further comprises a temperature sensor 26 in the cavity 11 for monitoring the temperature of the sample. In these preferred embodiments, the first and second fans 20,21 are controllable variable speed fans. In these embodiments, the apparatus further comprises a controller 27 that moderates the draw of the first fan 20, the second fan 21, or both, based upon the sample temperature measured by the temperature sensor 26. As will be described herein with respect to the method aspects of the invention the ability to control the airflow based upon the particular stage of heating, combustion, or cooling, can speed the analysis considerably. The temperature sensor can be selected as desired based on a number of engineering criteria, but will typically comprise a thermometer, a thermocouple or an optical temperature measuring device. It will be understood that the particular device used to measure the temperature is in no manner limiting of either the apparatus or method of the present invention.

Controllers and their method of operation are generally well-understood in this art and will not be described in detail herein. Exemplary devices and techniques are set forth, for example, in Dorf, *The Electrical Engineering Handbook*, Second Edition, CRC Press (1997).

Because this particular embodiment of the invention uses microwave heating, it further comprises the housing 30 shown in FIG. 1 that is formed of a material, typically metal, that surrounds the cavity 11 and the ceramic furnace material 18 to shield the external surroundings from the microwaves that are propagated into the cavity 11 by the magnetron 14 and the waveguide 15. Any materials that will suitably shield microwaves are appropriate for the housing 30, but metal is typically used under most circumstances. The housing 30 also defines a ventilation opening 31 through which air can flow into the space between the housing 30 and the furnace ceramic material 18. In this embodiment, the second fan 21 is positioned to draw an airflow into the space between the housing 30 and the cavity 21. Because this airflow starts from an ambient source, and does not pass through the combustion chamber, it generally serves to moderate the high temperatures on the exterior of the cavity generated by the combustion taking place inside. As in the case of the choke 19, the opening 31 (which is not drawn to scale) is either of a size that prevents microwaves from escaping therethrough, or includes an appropriately sized choke of its own.

FIG. 1 further illustrates a furnace exhaust pipe 32 that is in communication with the afterburner 17 and the first fan 20, and a housing exhaust pipe 33 that is in communication with the housing 30 and the second fan 21. The exhaust pipes 32 and 33 merge at a junction 34 to form a common exhaust designated by the arrows 35 for both of the fans. In preferred embodiments, the apparatus 10 includes an ambient air stem 36 in communication with the furnace exhaust pipe 32 which helps draw additional ambient air that blends with the furnace exhaust to help reduce its temperature.

FIG. 1 also illustrates that in the preferred embodiment, the housing exhaust pipe 33 has portions that are large enough for a smaller portion of the furnace exhaust pipe 32 to be positioned therein in generally concentric fashion (when the pipes are circular). In this manner, the generally cooler air that the second fan 21 draws into the housing 30 and through the housing exhaust pipe 33, cools the generally much hotter gaseous byproducts from the furnace 18 and the afterburner 17 that travel through the furnace exhaust pipe 32. Thus, the invention provides an apparatus and method for drawing one airflow through the furnace 18 and into the furnace exhaust 32 while concurrently drawing another, separate airflow through the housing 30 and into the housing exhaust 33, and then joining the exhausts to form a common exhaust from both the housing 30 and the furnace 18.

It will be understood that a single fan, if positioned appropriately downstream, can draw the separate airflows, but in preferred embodiments the two separate fans 20 and 21 are incorporated. In the preferred embodiments, the fans 20 and 21 are each located upstream from the junction 34 (with downstream referring to the exit portions of the exhaust) although other arrangements in the positioning of the fans are appropriate provided the airflows are drawn in the manner of the invention.

Figure 2:
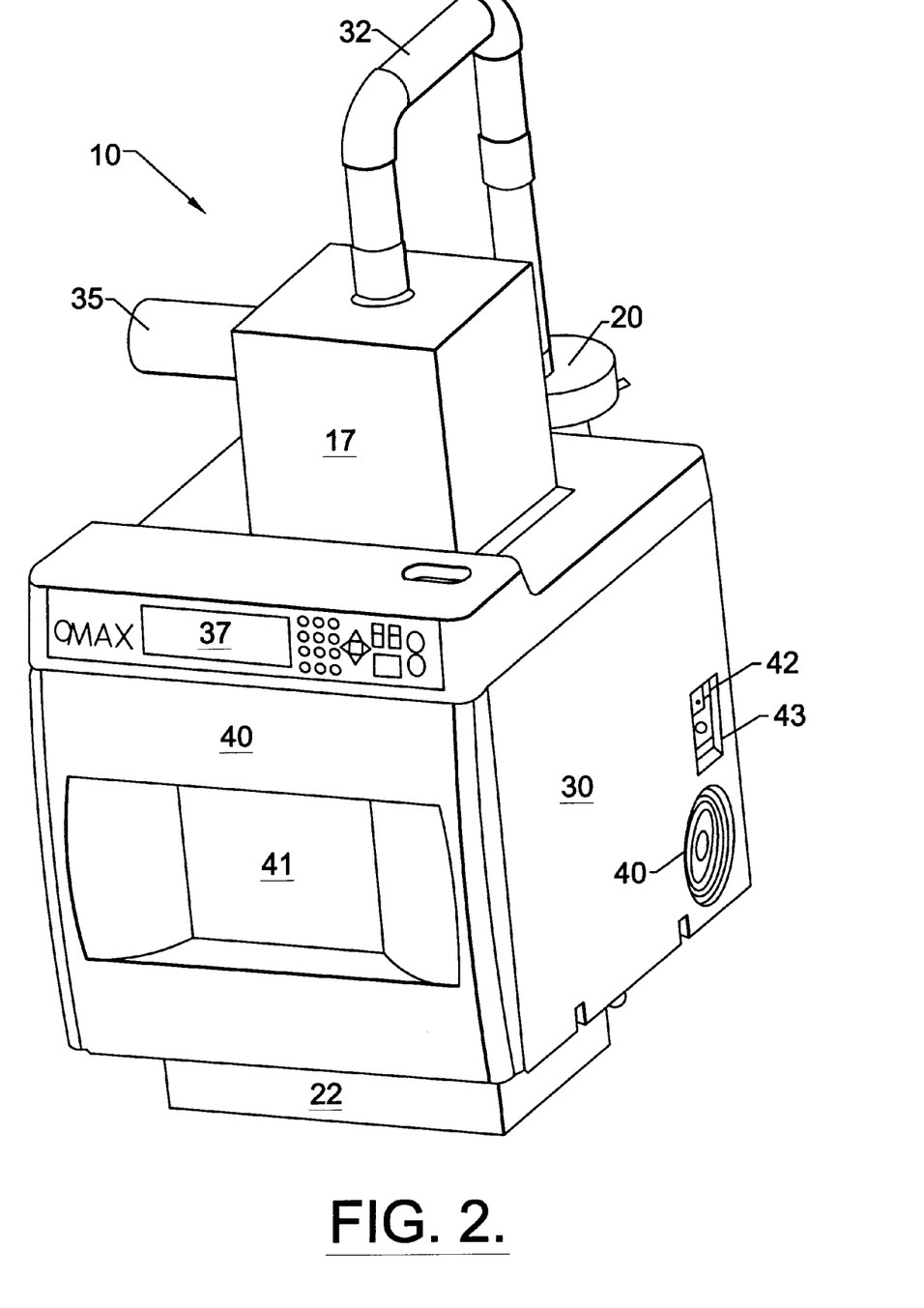
FIG. 2 is a front perspective view of a commercial embodiment of the invention.
Figure 3:
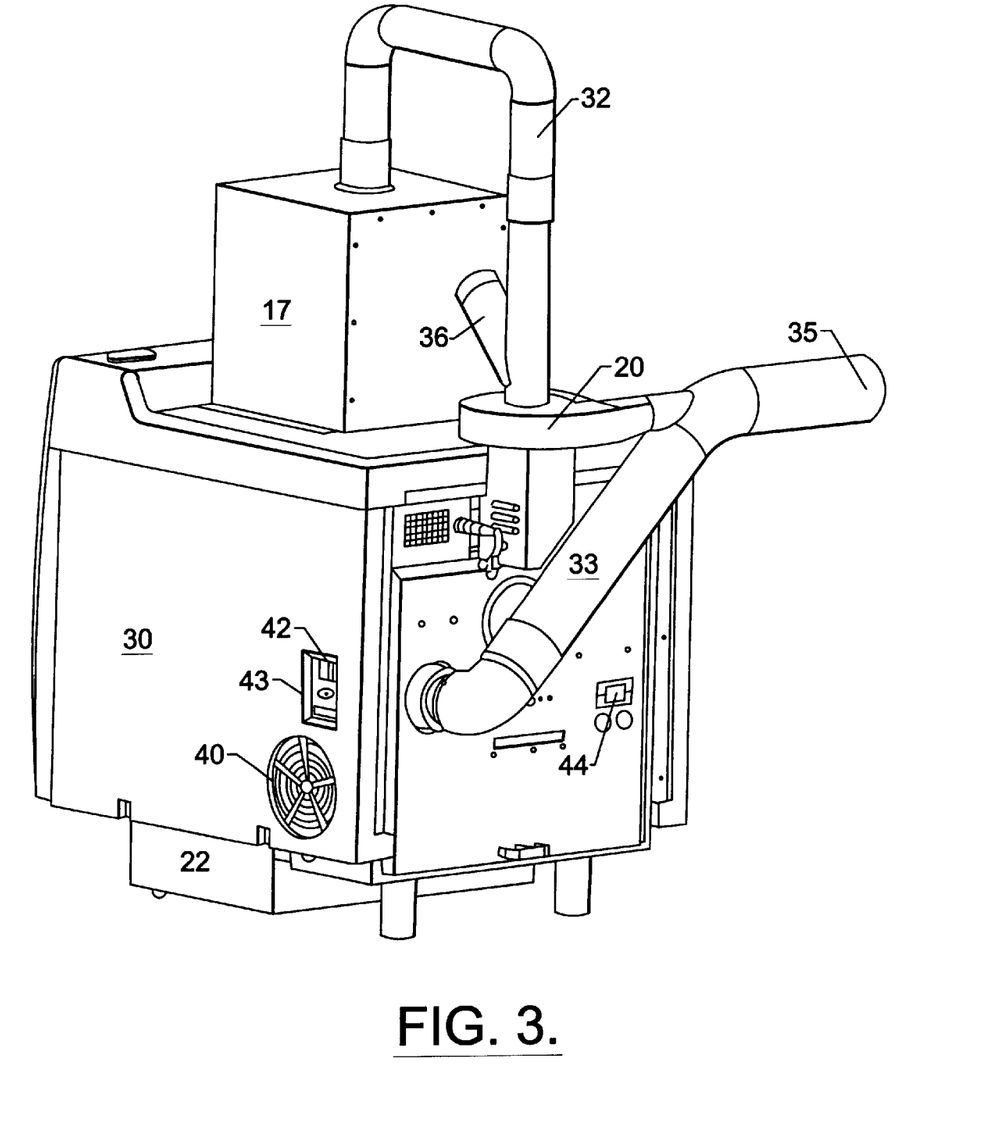
FIG. 3 is a rear perspective view of the embodiment illustrated in FIG. 2.

FIGS. 2 and 3 show some of these same elements in a more realistic and less schematic illustration. In FIG. 2 the apparatus 10 includes the overall housing 30, the housing for the scale 22, the afterburner 17, the furnace exhaust pipe 32, and the common exhaust 35.

FIG. 2 also illustrates a control panel 37, the first fan 20, and a third fan 40 which is used to cool the electronic portions of the device rather than the airflow from the furnace or the housing.

As in many microwave devices, the housing 30 includes a door 40 for providing access to the furnace therein, as well as a window 41 that permits portions of the interior to be visible from the exterior of the housing 30. FIG. 2 also illustrates a basic power switch 42 and connections for exchanging data (e.g. parallel and serial connectors) 43.

FIG. 3 illustrates many of the same elements as 1 and 2, but from a rear perspective view. In addition to those elements already recited with respect to FIG. 2, FIG. 3 shows the ambient air stem 36 and the housing exhaust pipe 33. The second fan 21 is generally interior to the housing in these embodiments, and thus not visible in FIGS. 2 or 3. FIG. 3 also shows a power connector 44 for providing current to the device from a typical commercial or industrial line.

The apparatus aspects of the invention compliment the method. In its basic aspects, the method of the invention comprises heating a furnace with a preweighed container carrying a sample of an asphalt-aggregate composition therein while drawing air through the furnace at a rate that avoids impeding the heating of the furnace or the sample until the sample in the container reaches its combustion point and the combustion of the sample becomes exothermic. At that point, the draw of airflow through the furnace is accelerated to increase the rate of combustion of the exothermic reaction until the exothermic reaction is complete. Thereafter, the container and sample are re-weighed.

With respect to weighing the sample, it will be understood both from the apparatus aspects of the invention and from the techniques described in parent application Ser. No. 09/045,392 that in preferred embodiments, the container and sample are continuously weighed during the heating and combustion processes. As further set forth in the parent application, after the aggregate has been cooled, it is preferably sized to provide the useful information about the aggregate that is the desired end product of the overall analysis.

As described with respect to the apparatus aspects, the method preferably further comprises initiating a second draw of air around rather than through the furnace to moderate the exterior of the furnace. In typical operation, the method comprises weighing the sample and its container before placing it in the furnace and also preheating the sample and container prior to placing them in the furnace. In the preferred embodiments, the furnace is preheated to a temperature higher than the preheated temperature of the container and sample. In typical embodiments, the container and sample are heated to a temperature of about 150° C. prior to placing them in the furnace, while the furnace is typically heated to a temperature above about 540° C. prior to placing the container and sample therein.

As in the apparatus aspects of the invention, the step of heating the furnace preferably comprises directing microwave radiation at microwave absorbent materials in the furnace that convert the microwave energy into heat.

In another aspect, the step of heating the furnace while drawing air therethrough can comprise heating the sample until it reaches a first predetermined setpoint temperature and then accelerating the draw through the furnace to increase the rate of combustion of the sample. In this embodiment, the method preferably also comprises initiating the second draw of air around rather than through the furnace when the temperature reaches a second predetermined setpoint. In the most preferred embodiments, the second predetermined setpoint temperature is lower than the first predetermined setpoint temperature so that the second draw of air around the furnace is typically initiated prior to the acceleration of the draw through the furnace. As exemplary, but not limiting temperatures, the external draw of air through the housing is initiated when the temperature of the sample and container reach about 480° C., and the furnace draw is accelerated when the temperature reaches about 500° C. The temperature is monitored throughout the process, and preferably continuously.

In another aspect, the method comprises heating a sample of the asphalt-aggregate composition in the furnace, drawing an airflow into, through, and out of the furnace to promote the combustion of the asphalt in the composition, drawing a separate airflow around and past, but not through, the furnace to help moderate the exterior temperature of the furnace without interfering with the combustion therein, and blending the airflow that has exited the furnace with the airflow that has passed the exterior to thereby moderate the temperate of the furnace exited airflow.

In this embodiment, the method preferably further comprises blending an ambient airflow with the furnace-exited airflow, and thereafter blending again with the exterior airflow. As in the prior embodiments, the step of drawing the airflow out of the furnace preferably comprises drawing the airflow and gaseous combustion products from the furnace into the afterburner prior to blending it with the exterior airflow.

In operation to date, the apparatus and method of the invention appear to reduce the time required to conduct the combustion portion of an asphalt-aggregate analysis by at least about 40%. As set forth in the parent application, one of the advantages of faster analysis of asphalt-aggregate compositions is the ability to get information about the composition as soon as possible after the composition has been sampled. In that manner, any changes required in the aggregate mix or the aggregate asphalt composition can be made as quickly as possible.

As noted above, one of the most important characteristics of an asphalt-aggregate composition is the particle size distribution of the aggregate materials. Thus, the method of the invention further comprises sizing the aggregate after combustion of the asphalt. In particular, the nature of the combustion process according to the invention provides a less distorted and frequently undistorted aggregate for which the sizes and size distribution can be more accurately determined.

In typical embodiments, the step of sizing the aggregate comprises sieve analysis (e.g., U.S. standard sieve sizes), but it will be understood that any appropriate sizing technique can be used with the present invention and that the invention provides the advantage of maintaining the aggregate in its original size following combustion much more successfully than have prior ignition techniques.

Because asphalt-aggregate compositions can vary so widely depending on a variety of factors, objective determinations of post-combustion aggregate quality can be difficult. Nevertheless, the appearance of the post-combustion aggregate can provide a qualitative measure of the success of the method in preserving the aggregate as closely as possible to its pre-combustion condition. In this regard, the post-combustion samples from asphaltaggregate compositions analyzed according to the present invention give every indication of being in better—i.e. close or identical to pre-combustion—condition that samples analyzed using more conventional ignition techniques. It is thus expected that any objective evaluation of such post-combustion samples will similarly demonstrate the advantages of the present invention in properly preserving the aggregate.

In summary, the invention provides a more controllable method of carrying out an ignition and combustion analysis of asphalt-aggregate compositions and does so in a manner that minimizes or avoids the degradation of the aggregate that is commonly observed in conventional ignition and combustion testing.

In the drawings and specification, there have been disclosed typical embodiments of the invention, and, although specific terms have been employed, they have been used in a generic and descriptive sense only and not for purposes of limitation, the scope of the invention being set forth in the following claims.

That which is claimed is:

1. A method of analyzing the aggregate content of asphalt-aggregate compositions, the method comprising:
heating a furnace with a preweighed container carrying a sample of an asphalt-aggregate composition therein by directing microwave radiation at microwave adsorbent materials in the furnace;
initiating a first draw of air through the furnace at a rate that avoids impeding the heating of the furnace or the sample until the sample in the container reaches combustion and the combustion of the sample becomes exothermic;

initiating a second draw of air around rather than through the furnace to moderate the exterior temperature of the furnace and prevent an uncontrolled temperature rise in the furnace and the sample;

moderating the first draw of air through the furnace to increase the rate of combustion of the exothermic reaction until the exothermic reaction is complete; and reweighing the container and sample after combustion is complete.

2. An analysis method according to claim 1 comprising weighing the container and sample and thereafter placing the container and sample in the furnace.

3. An analysis method according to claim 2 comprising preheating the container and sample prior to placing the container and sample in the furnace.

4. An analysis method according to claim 3 comprising preheating the furnace prior to placing the container and sample in the furnace.

5. An analysis method according to claim 4 comprising preheating the furnace to a temperature higher than the preheated temperature of the container and sample.

6. An analysis method according to claim 1 comprising weighing the container and sample while the container and sample are in the furnace and while the furnace is being heated.

7. An analysis method according to claim 1 comprising continuously weighing the container and sample.

8. An analysis method according to claim 1 and further comprising sizing the aggregate after combustion of the asphalt.

9. A method of analyzing the aggregate content of asphalt-aggregate compositions, the method comprising:

placing a preheated, preweighed container carrying a sample of an asphalt-aggregate composition into a preheated furnace with the preheated furnace being warmer than the preheated sample;

continuing to heat the furnace by directing microwave radiation at microwave adsorbent materials in the furnace;

initiating a first draw of air through the furnace at a rate that avoids impeding the heating of the furnace or the sample until the sample in the container reaches its combustion temperature and the combustion of the sample becomes exothermic;

initiating a second draw of air around rather than through the furnace to moderate the exterior temperature of the furnace;

moderating the first draw of air through the furnace to increase the rate of combustion of the exothermic reaction; and reweighing the container and sample after combustion is complete.

10. An analysis method according to claim 9 comprising weighing the container and sample prior to placing the container and sample in the furnace.

11. An analysis method according to claim 9 comprising preheating the container and sample to a temperature of about 150° C. prior to placing the container and sample in the furnace.

12. An analysis method according to claim 11 comprising preheating the furnace to a temperature above about 540° C. prior to placing the container and sample in the furnace.

13. An analysis method according to claim 9 comprising weighing the container and sample while the container and sample are in the furnace and while the furnace is being heated.

14. An analysis method according to claim 13 comprising continuously weighing the container and sample.

15. An analysis method according to claim 9 and further comprising sizing the aggregate after combustion of the asphalt.

16. A method of analyzing the aggregate content of asphalt-aggregate compositions, the method comprising:

placing a preheated, preweighed container carrying a sample of an asphalt-aggregate composition into a preheated furnace;

monitoring the temperature of the furnace;

continuing to heat the furnace by directing microwave radiation at microwave adsorbent materials in the furnace;

initiating a first draw of air through the furnace at a rate that avoids impeding the heating of the furnace or the sample until the sample in the container reaches a first predetermined setpoint temperature;

initiating a second draw of air around rather than through the furnace to moderate the exterior temperature of the furnace when the temperature reaches a second predetermined setpoint;

moderating the first draw of air through the furnace to increase the rate of combustion of the sample; and reweighing the container and sample after combustion is complete.

17. An analysis method according to claim 16 wherein the second predetermined setpoint temperature is lower than the first predetermined setpoint temperature so that the second draw of air around the furnace is initiated prior to the moderation of the draw through the furnace.

18. An analysis method according to claim 16 comprising weighing the container and sample while the container and sample are in the furnace and while the furnace is being heated.

19. An analysis method according to claim 18 comprising continuously weighing the container and sample.

20. An analysis method according to claim 16 comprising preheating the furnace to a temperature warmer than the preheated sample.

21. An analysis method according to claim 16 and further comprising sizing the aggreaate after combustion of the asphalt.

22. An apparatus for analyzing the aggregate content of asphalt-aggregate compositions and comprising:

a cavity for holding an asphalt-aggregate sample;

means for introducing microwave radiation into said cavity;

materials in said cavity for absorbing microwave radiation and converting the microwave radiation into heat;

an afterburner in gas flow communication with said cavity;

a first controllable variable speed fan for drawing air through said cavity and through said afterburner;

a second controllable variable speed fan for drawing air around said cavity to moderate the external temperature of said cavity and its immediate environment;

a temperature sensor in said cavity for monitoring the temperature of the sample;

a controller that moderates the draw of said first fan based upon the sample temperature measured by said temperature sensor; and a controller that moderates the draw of said second fan. aggregate after combustion of the asphalt.

23. An analysis apparatus according to claim 22 and further comprising a scale in said cavity for continuously monitoring the weight of a sample in said cavity.

24. An analysis apparatus according to claim 22 comprising a housing surrounding said cavity.

25. An analysis apparatus according to claim 24 wherein said second fan is positioned to draw an airflow between said cavity and said housing.

26. An analysis apparatus according to claim 22 wherein said cavity is formed of a material that is insulating with respect to conductive heat transfer and substantially transparent to microwave radiation.

27. An analysis apparatus according to claim 26 wherein said cavity is formed of a glass ceramic fibrous material.

28. An analysis apparatus according to claim 22 wherein said microwave introducing means comprises a source and a waveguide.

29. An analysis apparatus according to claim 22 comprising a susceptor in said furnace for absorbing microwave radiation and converting it into heat.

30. An asphalt analysis furnace system that enhances the airflow and combustion of asphalt-aggregate compositions, said furnace system comprising:

a furnace, that include a source of microwave radiation and a susceptor for absorbing the microwave radiation and converting it into heat;

a housing around said furnace;

a furnace exhaust in communication with said furnace;

a housing exhaust in communication with said housing;

means for drawing an airflow though said furnace and into said furnace exhaust;

means for drawing a separate airflow though said housing and into said housing exhaust; and a junction between said exhausts that forms a common exhaust from said housing and said furnace.

31. An analysis system according to claim 30 wherein said furnace drawing means and said housing drawing means comprises a single fan downstream from said junction.

32. An analysis system according to claim 30 wherein said furnace drawing means comprises a first fan in communication with said furnace exhaust upstream from said junction and said housing drawing means comprises a second fan in communication with said housing exhaust upstream from said junction.

33. An analysis system according to claim 30 and further comprising an afterburner between said furnace and said furnace exhaust.

34. An asphalt analysis furnace system that enhances the airflow and combustion of asphalt-aggregate compositions, said furnace system comprising:

a furnace, that includes a source of microwave radiation and a susceptor for absorbing the microwave radiation and converting it into heat;

a housing around said furnace;

a first fan that pulls air though said furnace;

a second fan that pulls air between said furnace and said housing, but not through said furnace;

a furnace exhaust pipe in communication with said first fan;

a housing exhaust pipe in communication with said second fan; and a junction between said exhaust pipes that forms a common exhaust for both of said fans.

35. A furnace system according to claim 34 comprising an ambient air stem in communication with said furnace exhaust pipe.

36. A furnace system according to claim 34 and further comprising an afterburner between said furnace and said furnace exhaust pipe.

37. A method of analyzing the aggregate content of asphalt-aggregate compositions, the method comprising:

heating a sample of an asphalt-aggregate composition to combustion in a furnace by directing microwave radiation into the furnace;

drawing an airflow into, through, and out of the furnace to promote the combustion of the asphalt in the composition;

drawing a separate airflow around and past but not through the furnace to help moderate the exterior temperature of the furnace without interfering with the combustion therein; and blending airflow that has exited the furnace with the airflow that has passed the exterior to thereby moderate the temperature of the furnace-exited airflow.

38. An analysis method according to claim 37 and further comprising blending an ambient airflow with the furnace-exited airflow.

39. An analysis method according to claim 38 comprising blending the ambient and furnace-exited airflows, and thereafter blending with the exterior-passed airflow.

40. An analysis method according to claim 37 wherein the step of drawing the airflow out of the furnace comprises drawing the airflow and gaseous combustion products into an afterburner prior to blending with the exterior airflow.

41. An analysis method according to claim 37 wherein the step of directing the microwave radiation into the furnace comprises directing the radiation to a susceptor that absorbs the microwave radiation and converts it into heat.

42. An analysis method according to claim 37 and further comprising sizing the aggregate after combustion of the asphalt.

* * * * *